(12) United States Patent
Bolmsjö et al.

(10) Patent No.: US 7,041,090 B2
(45) Date of Patent: May 9, 2006

(54) METHOD AND APPARATUS FOR SELF-DRAINING OF URINE

(75) Inventors: Magnus Bolmsjö, Lund (SE); Sonny Schelin, Rockneby (SE)

(73) Assignee: Prostalund Operations AB, Lund (SE)

( * ) Notice: Subject to any disclaimer, the term of this patent is extended or adjusted under 35 U.S.C. 154(b) by 360 days.

(21) Appl. No.: 10/415,616

(22) PCT Filed: Oct. 12, 2001

(86) PCT No.: PCT/SE01/02219

§ 371 (c)(1),
(2), (4) Date: Apr. 28, 2003

(87) PCT Pub. No.: WO02/36192

PCT Pub. Date: May 10, 2002

(65) Prior Publication Data

US 2004/0097891 A1    May 20, 2004

Related U.S. Application Data

(63) Continuation-in-part of application No. 09/704,223, filed on Nov. 1, 2000, now Pat. No. 6,626,876.

(51) Int. Cl.
*A61M 1/00* (2006.01)
*A61M 27/00* (2006.01)
*A61M 31/00* (2006.01)

(52) U.S. Cl. ............... 604/327; 604/544; 604/95.04; 604/530

(58) Field of Classification Search ............ 604/93.01, 604/95.04, 104, 154, 171, 174, 517, 327, 604/544, 317, 349
See application file for complete search history.

(56) References Cited

U.S. PATENT DOCUMENTS

| 4,790,810 A | 12/1988 | Pugh, Jr. et al. |
| 5,176,664 A | 1/1993 | Weisman |
| 5,489,269 A * | 2/1996 | Aldrich et al. ........... 604/95.04 |
| 5,738,654 A | 4/1998 | Tihon |
| 5,941,849 A * | 8/1999 | Amos et al. ............. 604/95.04 |
| 6,048,329 A * | 4/2000 | Thompson et al. ...... 604/95.04 |
| 6,368,340 B1 | 4/2002 | Malecki et al. |
| 6,524,268 B1 * | 2/2003 | Hayner et al. .................. 604/8 |

(Continued)

FOREIGN PATENT DOCUMENTS

EP        0 542 246 A1 *    5/1993

(Continued)

OTHER PUBLICATIONS

Search report for WO 02/36192 A1, May 2002, WIPO.*

(Continued)

*Primary Examiner*—Tatyana Zalukaeva
*Assistant Examiner*—Michael G Bogart
(74) *Attorney, Agent, or Firm*—John R. Ley

(57) ABSTRACT

A device for the drainage of the bladder through the body's own urethra opening outside of the human body, comprising a tube-shaped body (10). The 5 tube-shaped body is comprised: to assume a first contracted position and for taken up within the bladder as well as a to assume a second partially extended position. At least one thread (14) extends between the bladder and an opening so that the tube-shaped body can be extended from the first position to the second position during 10 the application of a pulling force upon the thread. The tube-shaped body will return to the first position upon the release of the pulling force on the thread.

25 Claims, 5 Drawing Sheets

U.S. PATENT DOCUMENTS

| | | | |
|---|---|---|---|
| 6,626,876 B1 * | 9/2003 | Bolmsjo et al. | 604/317 |
| 6,648,863 B1 * | 11/2003 | Reever | 604/327 |
| 6,656,146 B1 * | 12/2003 | Clayman et al. | 604/8 |
| 2001/0049490 A1 * | 12/2001 | Slanda et al. | 604/95.04 |
| 2002/0004644 A1 * | 1/2002 | Koblish | 604/104 |
| 2003/0191450 A1 * | 10/2003 | Teague et al. | 604/524 |

FOREIGN PATENT DOCUMENTS

| | | |
|---|---|---|
| EP | 0 733 379 A1 * | 9/1996 |

OTHER PUBLICATIONS

Kapoor et al., *Do Prostatic Stents Solve the Problem of Retention after Transurethral Microwave Thermotherapy?*, Journal of Endurology, vol. 14, No. 8, Oct. 2000, pp. 683-687.

* cited by examiner

METHOD AND APPARATUS FOR SELF-DRAINING OF URINE

CROSS-REFERENCE TO RELATED APPLICATION

This is a continuation in part of U.S. application Ser. No. 09/704,223, filed Nov. 1, 2000 by the inventors hereof, now U.S. Pat. No. 6,626,876 issued Sep. 30, 2003.

FIELD OF THE INVENTION

Prostate problems, such as benign prostate hyperplasia (BPH) or prostate cancer are usual occurrences among men. In many cases the symptoms experienced are very troublesome. Problems relating to the discharge of urine arise when the prostate gland swells to the extent that the urine duct, urethra, which runs through the prostate gland, is obstructed or pinched. The result of this process can lead to difficulties for the patient in being able to discharge urine at will, so-called urinary tract retention. Urinary tract retention can be either acute or chronic.

BACKGROUND OF THE INVENTION

The means for treating symptoms of urine retention is either surgery or another equivalent treatment, which removes the obstruction. Alternatively, the patient is required to have a catheter implanted or to learn so called self-draining. In the first case, a drainage catheter is placed into the urinary tract, from the penis and up into the bladder. The catheter is formed as a tube or a canal and is usually comprised of soft material, for example, latex, polyurethane, or silicone. At the end that lies in the bladder, the catheter is comprised of a balloon, which is blown up and prevents the catheter from slipping out. At the other end, outside of the penis, a clamp is usually attached so that the patient can open/close the catheter canal. Also urine can be collected by means of the attachment of a reservoir. The patient can also be taught to insert, on his own, a drainage catheter for him or herself into the bladder every time the urge to urinate arises and in that way can avoid the need to continually leave the catheter inside of him or herself.

There are a number of different forms of treatment with respect to obstruction by the prostate gland, such as surgery and treatment with heat. Aging problems in the form of acute urinary tract retention can arise, however, usually during a certain time after the treatment.

As relates to disease of the prostate, the type of assistance that is available today to many of those patients who have significant problems, and who no longer can rid themselves of urine spontaneously, is chronic catheter care in the form of continual use of a catheter. Alternatively, patients can be taught the technique of inserting an emptying catheter up through the urethra into the bladder every time the urge to urinate arises. However the patient must then always carry on his or her person sterile one-time use catheters. In certain more unusual cases, a stent can be placed into the prostate in order to stretch the tissue outward and allow the passage of urine. In the greatest majority of cases, however, a catheter is used. Disadvantages with all forms of catheter treatments, whether one uses an unremovable catheter or self-insertion, are that the patient's discomfort in using a catheter as well as the limitations on quality of life issues that come with it, i.e. socially, sexually, etc. In addition, there is a relatively high risk that urinary tract infections will arise through use of a catheter.

If the patient is determined to be an unsuitable subject to undergo a radical treatment of the disease by means such as surgery, due to weakness or other reasons use of a catheter will be required for the remainder of the patient's life.

Another usual form of treatment for obstructions caused by the enlargement of the prostate gland is by means of heat treatment using microwaves, radio waves, ultra sound or laser. The object of this type of treatment is to destroy a portion of the prostate tissue nearest to the urine through the urethra in order to achieve free passage of urine in this way. With such treatments, acute retention within the urinary tract usually arises. This is a result of the fact that the heat-treated prostate tissue becomes swollen. Thus, with respect to heat treatments, it is therefore quite usual that a catheter is inserted for approximately two weeks in order to insure the drainage of urine even during this period. Despite the fact that the drainage of urine is insured by using this method, the catheter in and of itself can result in problems for the patient.

SUMMARY OF THE INVENTION

One object of the present invention is to reduce the amount of displeasure experienced as a result of a patient's use of a catheter in association with the treatment of the prostate gland. Another object is to make possible the drainage of urine in association with other obstructions or another type of illness, for example, neurogenic bladder drainage disorders in women.

According to the invention there is introduced an elongated drainage body, such as a tube, a tube-shaped body, or a similar element that is coiled into one or more revolutions in the urine bladder in a first contracted position. The bends in the tube make it so that it cannot spontaneously slip out through the bladder neck. The tube is relatively soft so that it can be stretched out into an extended position if additional force is applied, and so that it will again assume its spiral shape if no outside force is applied. In the extended position it will function as a drainage catheter.

In one embodiment an elongated slit is formed in the elongated body to allow urine to leave the bladder and pass by the obstruction of the urethra. In one end of the body, a thread is attached. A free end of the thread runs out through the body's own urinary tract, which includes the urethra and penis/vagina. A small handle or stop can be made part of the thread in order to inhibit the end of the thread unintentionally receding into the urethra. In a second embodiment the elongated body is formed as a tube having a plurality of small perforations into which the urine can run.

When the patient experiences the urge to urinate, or for any other reason desires to empty the bladder, the patient pulls on the thread. The end of the body, which is attached to the thread is drawn down through the bladder, past the neck of the bladder and obstruction, and, in men, down through the prostate gland. The thread ought only be drawn to the extent that the end does not pass the apex of the prostate. Fittingly, a mark can be applied to the thread so that the treating doctor or nurse can designate how far the patient may draw so that the end will still remain inside of the prostate, yet will have passed the obstruction.

In such a manner, the patient can achieve drainage of the bladder. After drainage, the patient releases the thread, whereafter due to the spring mechanism or biasing force that is a result of the tube's winding spiral shape, the end will again be drawn in so that the entire tube lies in the bladder. The biasing force can be provided also by a stiffening wire attached to or embedded in the drainage body.

With the aid of the characteristics described in the invention, the tube is quite simple to apply, just as simple as inserting a normal drainage catheter.

It may be appropriate to provide the drainage body with a lubricating surface, so as to facilitate the insertion through the urethra. A preferred lubricating material is hydrogel but other materials with similar properties can be used.

As a result of the invention, a number of advantages are realized, among which are the following:

1. In the case that an obstruction that is hindering spontaneous emptying is of a temporary nature, for example after heat treatment, the patient himself will notice that he is again able to empty his bladder without means of assistance. He can then seek out medical assistance in order to remove the entire tube, or alternatively remove it himself.

2. The patient will experience a considerably lower degree of discomfort when he can avoid having a catheter inserted into the body or performing self-draining.

3. The risk of infection is likely to be considerably lower compared with catheter treatment.

4. The drainage will take place from within the bladder.

DETAILED DESCRIPTION OF PREFERRED EMBODIMENTS

Figure 1:
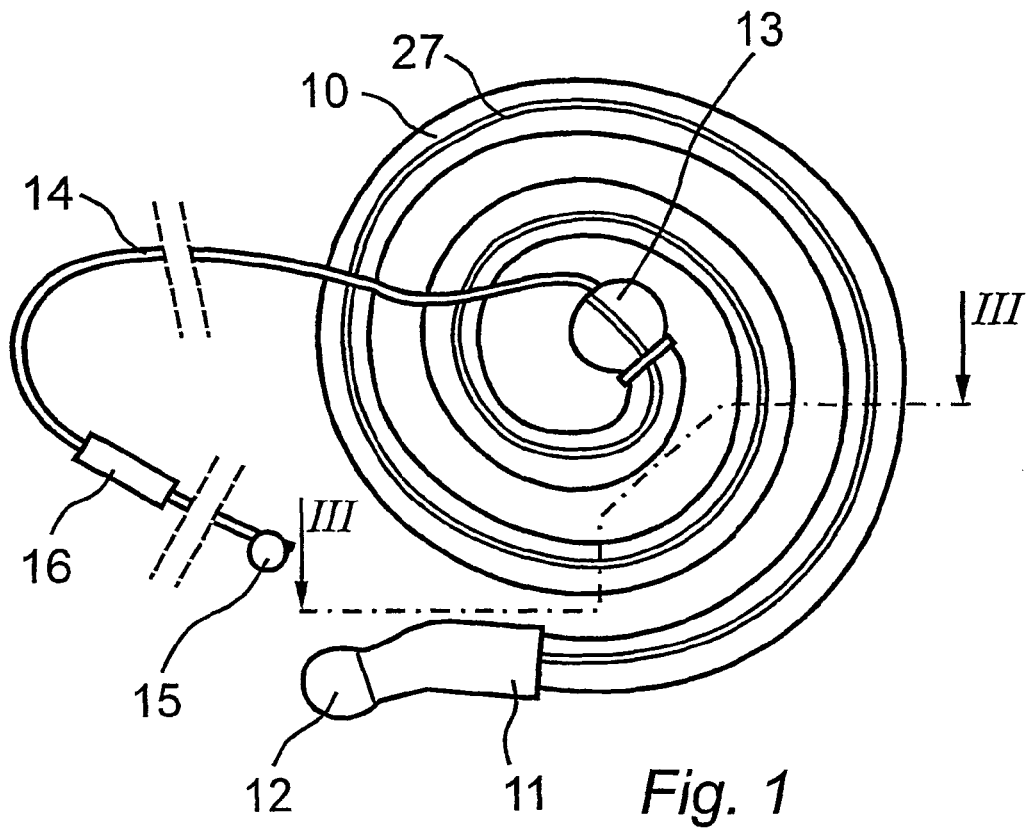
FIG. 1 shows a first embodiment of a device in accordance with the invention in a receding state.

In a first embodiment according to FIG. 1, an elongated body 10 functioning as a draining body has a first end that is attached with an end piece 11. The body 10 is formed as a flexible rod of silicon or polyurethane or a similar material and assumes, in one embodiment shown in FIG. 1, the drawn together, contracted or rolled-up form. The end piece 11 comprises a spherically formed ending 12, which makes possible the body's 10 introduction through the patient's urethra into the urine bladder. Through the application of a drawing pressure on the body 10, it can be caused to assume an extended form. A built in spring momentum, however, pulls the body 10 back to its contracted position when the pulling force is no longer applied.

In the embodiment shown in FIG. 1 the drainage body is formed with a slit 27 extending over a substantial part of the length of the drainage body. The slit 27 will allow urine to pass by the obstruction of the urethra when the drainage body 10 is in the extended position. This design of the drainage body can be manufactured in one step in a moulding process. By using silicon it is possible to produce the shape shown in FIG. 1 in one step, because it will release from the mould. Also other materials, such as polyurethane can be used. A stiffening wire (cf. FIG. 3) can be attached inside the slit 27 or be integrated with the drainage bode, so as to achieve an appropriate stiffness and a property to return to the contracted position.

A second end of the body 10 is formed of a special elastic or soft section 13. The soft section 13 is connected to a first end of a thread 14. The thread 14 is sufficiently long such that it, along with the entire tube-shaped body 10 introduced into the urine bladder, stretches itself out of the urinary canal of the patient. The urinary canal of a male patient is comprised of the urethra and the penis and for a female patient, the urethra and the vagina, more specifically, the entire distance from the urine bladder to the respective body opening.

Figure 16:
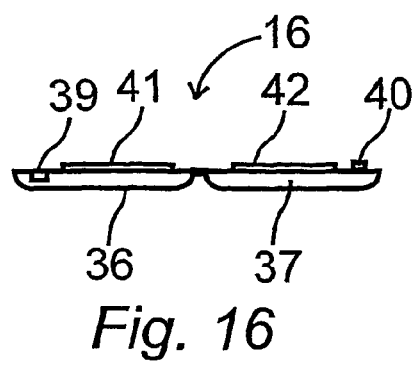
FIG. 16 is a schematic side elevational view of a marker for marking the position of the drainage body.
Figure 17:
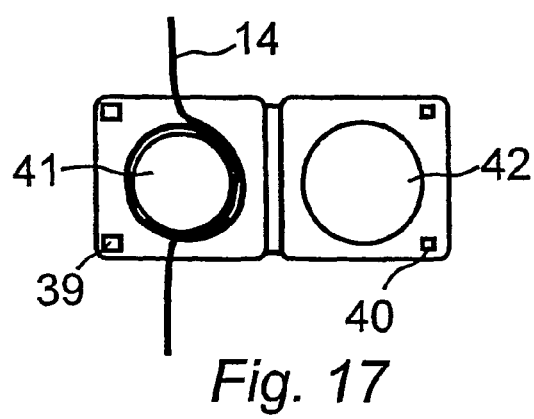
FIG. 17 is a plan view of the marker of FIG. 16.

At the thread's free end, there is a stop 15 in the form of a ball, or the like. After introduction of the body 10 into the urine bladder, the stop 15 prevents the thread from sliding into the urethra of the patient. A marker 16 on the thread makes it possible for the patient to control the drawing out of the thread 14 and body 10 to a suitable distance when used. An embodiment of the marker is shown in FIG. 16 and FIG. 17. Preferably the marker 16 is formed of a soft material. The use of the marker is described in more detail below as referenced in FIGS. 8–10.

Figure 2:
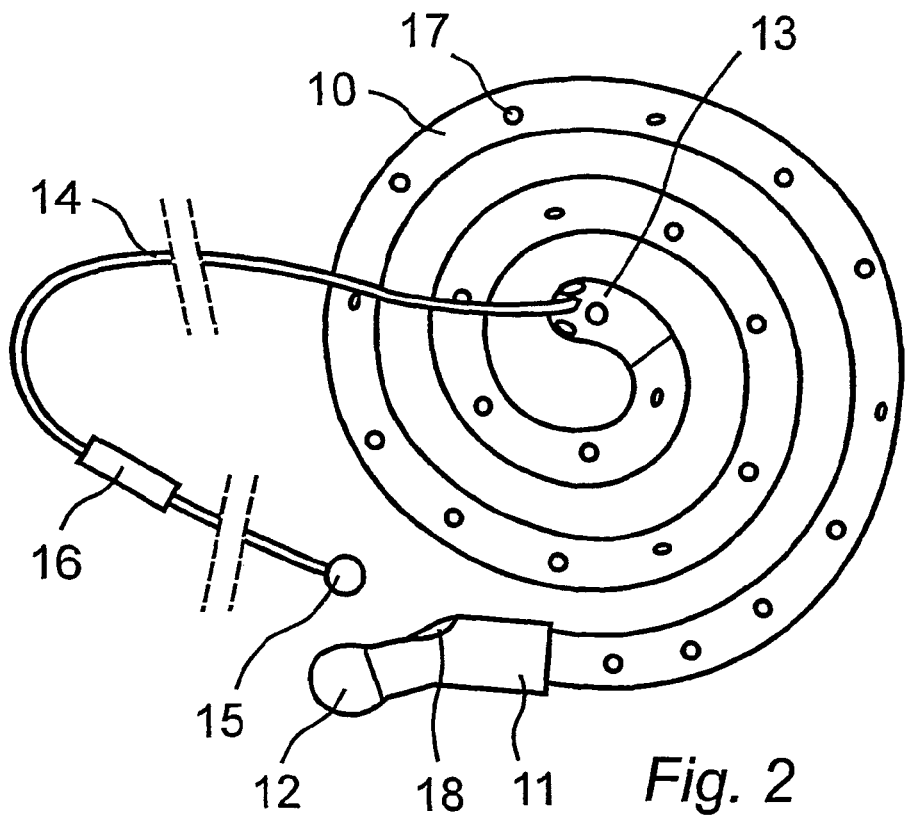
FIG. 2 shows a second embodiment of a device in accordance with the invention in a receding state.

In a second embodiment according to FIG. 2, a tube-shaped and extended body 10' has a first end that is attached with an end piece 11. The body 10' is formed as a flexible tube of polyurethane or similar material and assumes, in one embodiment shown in FIG. 2, the drawn together or rolled-up form. The end piece 11 is formed of a spherically formed ending 12, which makes possible the body's 10' introduction through the patient's urethra into the urine bladder. Through the application of a drawing pressure on the body 10', it can be caused to assume an extended form. A built in spring momentum, however, pulls the body 10' back to its contracted position when the pulling force is no longer applied.

The entire tube-shaped body is provided with a plurality of holes 17 that allows for the urine to run into the body's hollow inner space. The holes 17 are accordingly evenly distributed and are of such size that the risk of occlusion is small. A larger opening 18 is provided in the end piece 11 for the drainage of the urine bladder in association with the introduction of the body therein.

Figure 3:
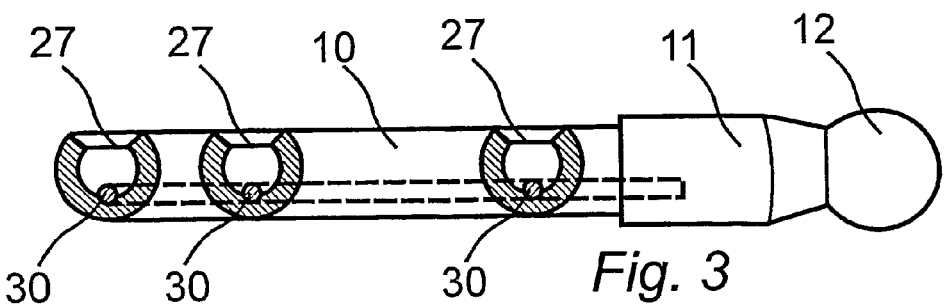
FIG. 3 is a sectional view from line III—III of the device in FIG. 1.
Figure 12:
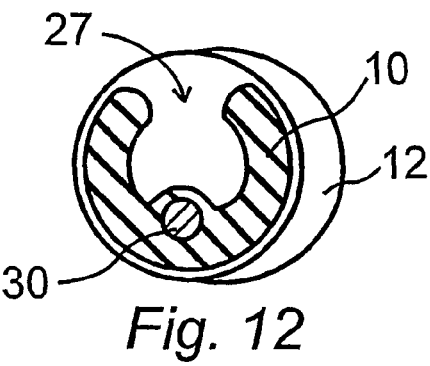
FIG. 12 is a cross sectional view of a first alternative embodiment of the device in accordance with the invention.
Figure 13:
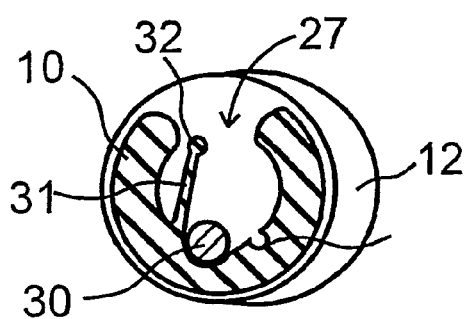
FIG. 13 is a cross sectional view of a second alternative embodiment of the device in accordance with the invention in a first position.
Figure 14:
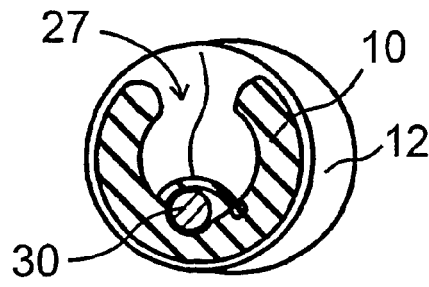
FIG. 14 is a cross sectional view of the device in FIG. 13 in a second position.

FIG. 3 is a sectional view of the device 10 shown in FIG. 1. The end piece 11 and the ending 12 are formed to facilitate the insertion of the device in the urethra and the bladder. The slit 27 will allow urine to enter the tube-shaped body when the device 10 is partly or completely within the bladder. A stiffening wire 30 is attached to or embedded in the drainage body. The stiffening wire will provide the device with an appropriate stiffness that will ensure that the device regains its contracted position after being extended. It is also possible to produce the drainage body from a material that will provide an appropriate stiffness without the stiffening wire. Other embodiments of the stiffening wire 30 are shown in FIG. 12 to FIG. 14. Preferably the stiffening wire 30 is inserted in and securely attached to the end piece 11 as shown in dashed lines.

The shape of the device can be accomplished in a one step moulding process if a suitable material such as silicone is used. Silicone will allow a negative angle on the forming tool because the adhesive forces are very low. The costs for producing the device by this method thus are very low.

Figure 4:
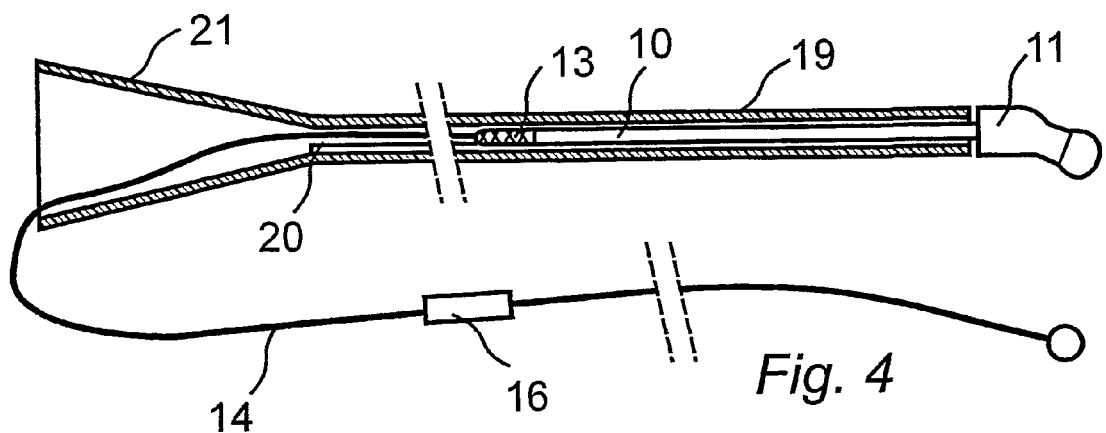
FIG. 4 shows the device in FIG. 2 in an extended state and introduced into an introducing member.

FIG. 4 depicts an introducing member 19. In the embodiment shown, the introducing member 19 is comprised of a flexible tube that is open at both ends. Accordingly, the introducing member 19 is comprised of polyurethane, polyethylene or a similar material. One end of the introducing member 19 comprises a conical part 21 for the purpose of making possible the introduction of a driving element (see description of FIG. 5). The conical part can also comprise a gripping means for the doctor or nurse who is using the device. In the center of the introducing member near the conical part, a guide thread 20 is attached. The guide thread 20 runs through the introducing member and makes it possible to eject the body 10 that has been placed within the introducing member 19.

In FIG. 4, the tube-shaped body 10 is introduced into the introducing member 19 and thereby extended to assume a second position. The insertion of the tube-shaped body 10 can be facilitated by the application of a thin layer of lubricating material such as a hydrogel. When water is applied the hydrogel layer will provide a very low friction. However, in its original state outside of the introducing member 19, the body 10 will attempt to reassume the shape as described in FIG. 2. The soft section 13 of the body 10 is positioned within the introducing member 19 so that it is turned against the conical part 21 while the end piece 11 extends outside of the introducing member 19. In this way the introducing member 19 and the tube-shaped body 10 together form a device that can be inserted through the urethra. The end piece 11 and the spherically formed ending 12 have a shape that will facilitate the insertion of the device through the urethra.

Figure 5:
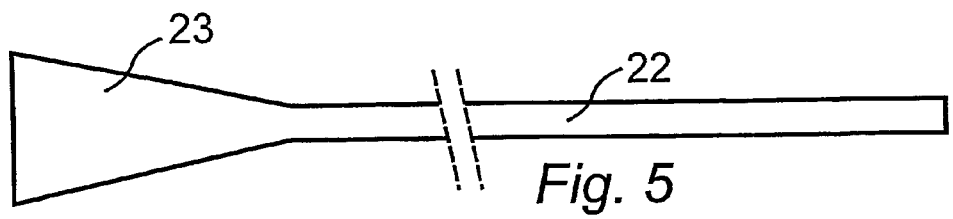
FIG. 5 shows a driving element that can be used to push the device in FIG. 2 out of the introducing member.

FIG. 5 displays one embodiment of a driving element 22. Preferably the driving element 22 is comprised of a conical section 23 corresponding to the conical part 21 of the introducing member 19. Also in this embodiment the conical section 23 can be used as a gripping means. The driving element 22 can also be formed from polyurethane or a material with similar properties.

Figure 6:
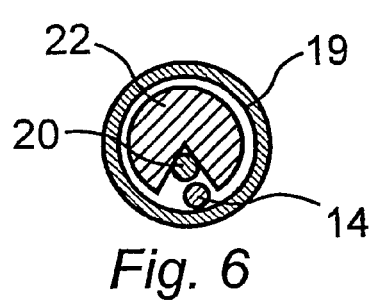
FIG. 6 is a cross-sectional view of the introducing member in FIG. 4 containing an already introduced first embodiment of a driving element.

FIG. 6 is a cross-sectional view, which shows the introducing member 19 wherein a first embodiment of the driving element 22 has been introduced. The driving element 22 has a circular cross-section with a receding slit for receiving a guide thread 20 and the thread 14. The driving element 22 is placed into the introducing member 19 when the introducing member is in the desired position with the end piece inserted into the bladder and with the driving element 22 pressing the tube-shaped body 10 into the urine bladder.

Figure 7:
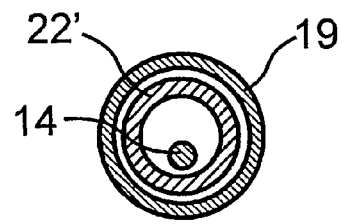
FIG. 7 is a cross sectional view of the introducing member in FIG. 4 containing an already introduced second embodiment of a driving element.

FIG. 7 is a cross sectional view, which shows the introducing member 19 along with an alternative and preferred embodiment of a driving element 22' introduced therein. The alternative driving element 22' is tube-shaped with a central inner cavity created for the purpose of drawing through it the thread 14. The guide thread 20 is not present in the embodiment shown according to FIG. 7 and is not required.

Prior to insertion, the thread 14 is drawn through the introducing member 19 so that the thread extends outwardly into the rear conical part 21. The thread also extends through the driving element 22, 22', so as to be available from the exterior. Thereafter the user pulls on the thread 14 so that the whole body 10, with the exception of the end piece 11, is drawn into the introducing member 19. If a guide thread 20 is used, the body 10 will follow the guide thread 20 and its position will be stretched out accordingly. The end piece 11 is preferably formed with the same outer diameter as the introducing member 19. As a final aspect of the preparation for the introduction, the driving element 22, 22' is guided into the introducing member 19 from its end possessing the conical part 21 until the driving element 22, 22' lies against the soft section 13 of the body 10. The introduction of the driving element 22, 22' can also be postponed to a later time.

In the above-described embodiment, the entire device is inserted in its full length through the urethra and up into the bladder. The introducing member 19 should also be of such length so that the end piece is ensured of being introduced into the urine bladder. In a simple manner, the end piece's position can be monitored by the fact that urine drains from the introducing member 19. The driving element 22 can therewith be drawn out of the introducing member 19, or be provided with channels running along its surface for the purpose of drawing away urine when the driving element 22 is inserted into the introducing member 19.

After ensuring that the end piece is correctly positioned, the full-length of the driving element 22, 22' is inserted into the introducing member 19, wherewith the body 10 passes into the bladder and assumes its contracted form. Thereafter the driving element 22, 22' along with the introducing member 19 are drawn completely out of the urethra. During removal of the driving element 22, 22' and the introducing member 19, the thread 14 should not be placed under any pressure, but should slide out freely through and from the introducing member 19 and the driving element 22'.

Figure 8:
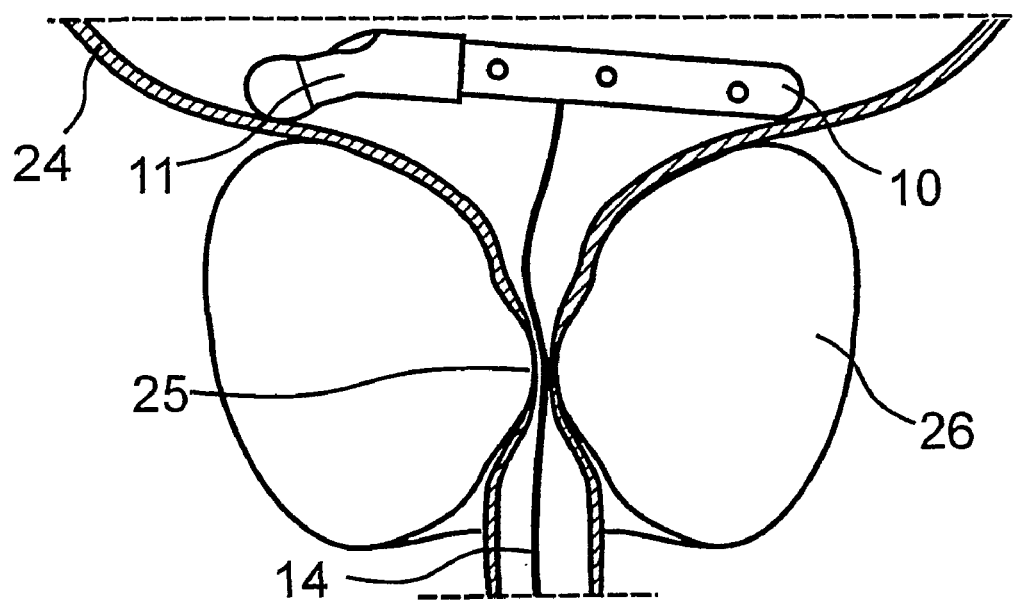
FIG. 8 shows a schematic view of the device in FIG. 2 fully introduced into a urine bladder.

FIG. 8 is a schematical view of the body 10' as introduced into the bladder 24 and with its end piece 11 resting against the urine bladder's wall. The thread 14 runs down through the point of the urethra's closing 25 and is accessible outside of the body. The point of the urethra's closing 25 is, as in the drawing provided, caused by the prostate tissue 26 that has been enlarged.

Figure 9:
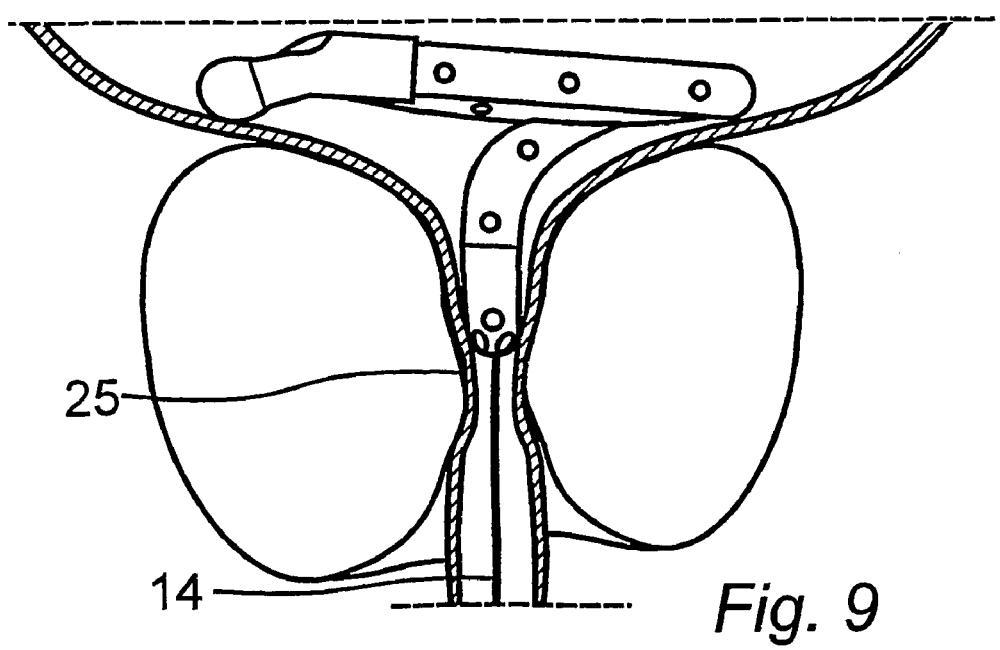
FIG. 9 shows the device in FIG. 8 extended to a first position partially drawn down into the urethra.
Figure 10:
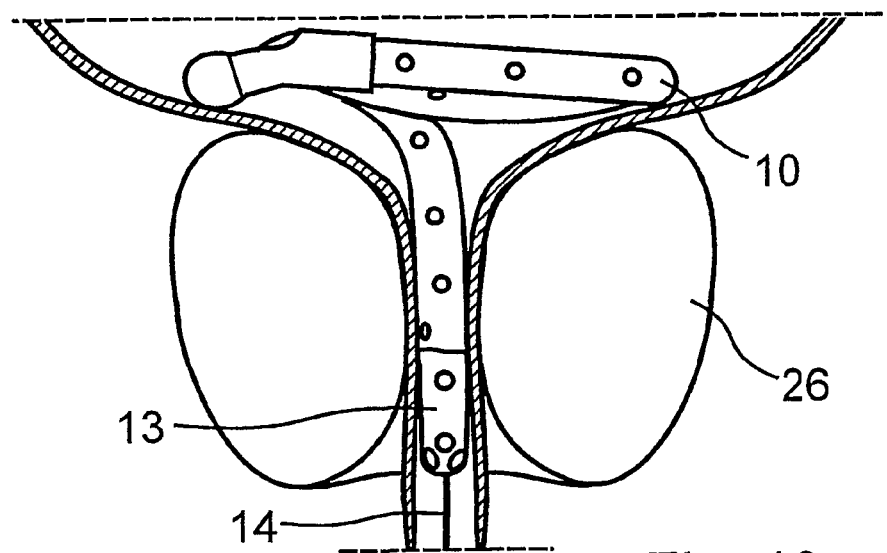
FIG. 10 shows the device in FIG. 8 extended to a second position drawn down into the urethra into such a position that the urine can freely flow out of the urine bladder.

When the urge to urinate arises or during other drainage of the bladder, the patient draws the thread 14, whereafter conditions in accordance with FIG. 9 will arise. The soft section 13 has been drawn down through the neck of the bladder and presses down upon tissue that is blocking the urethra when force is applied to the thread 14.

Additional drawing on the thread 14 results in the body 10' being drawn down through the prostate 26 and creates a canal, through which the patient can empty his bladder. These circumstances are exhibited in FIG. 10, where the soft section 13 has been completely drawn past the point of the urethra's closing 25. Urine can then freely pass through the tube-shaped body 10'. After drainage has occurred the thread 14 is released wherewith the body 10' slowly returns to the contracted position shown in FIG. 1, FIG. 2 and FIG. 8.

If the condition which has caused the point of the urethra's closing 25 abates, for example after a certain time subsequent to heat treatment of the prostate, the entire device can be removed by the patient simply drawing out the entire thread 14. The body 10' will then follow in the same path of removal without damaging the urethra or other tissue.

In addition to polyurethane other similar pliable materials can be used to form the tube-shaped body 10', the introducing member 19, and the driving element 22, 22'. An example of such material is silicone. The introducing member 19, however, should have a certain rigidity so that the tube-shaped body can be safely pushed through it.

Figure 11:
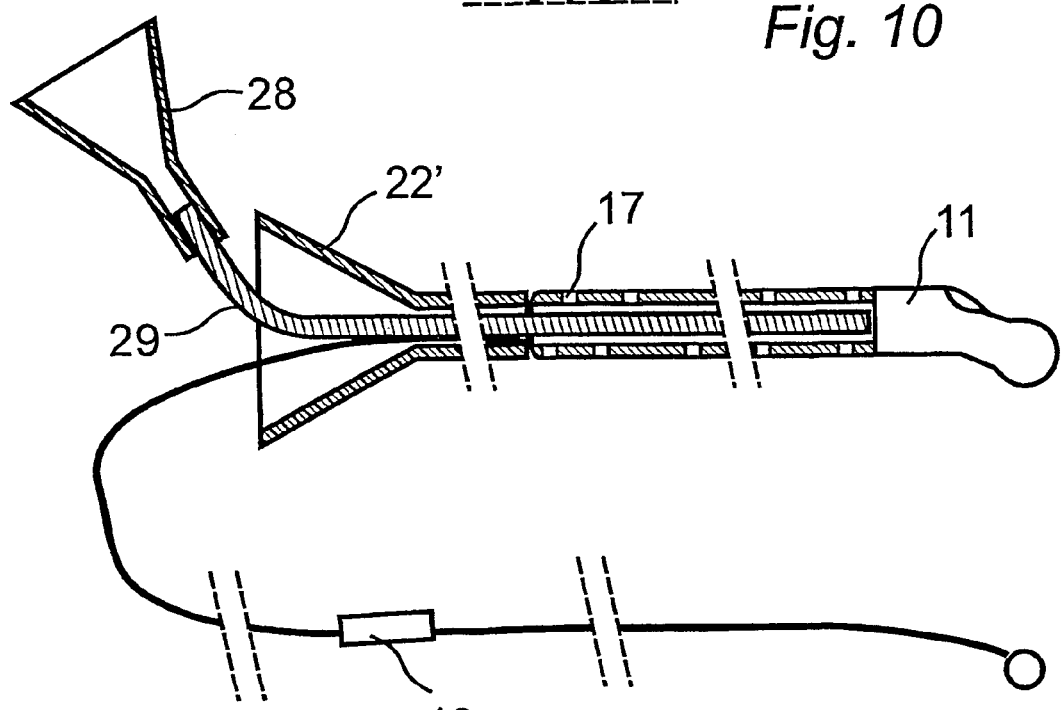
FIG. 11 is a schematic view drawing of an alternative embodiment of an introducing member.

In the embodiment according to FIG. 11, the introducing member is comprised so that a flexible guide thread 29 has an outer dimension less than the diameter of the tube-shaped body's 10 inner diameter. In order to facilitate the use of the introducing member, the thread 29 is provided with a gripping means 28. In the exhibited embodiment, a circular cross-section is used. The driving element 22' also in this embodiment is tube-shaped.

In the embodiment shown in FIG. 11 the driving element 22', like the entirety of the tube-shaped body 10, is guided via the flexible guide thread 29. Accordingly, the flexible guide thread 29 is extended throughout essentially the entirety of the tube-shaped body 10. One advantage of this embodiment is that the tube-shaped body 10 can be created to possess a greater outer diameter and therewith offer enhanced drainage capacities. The flexible guide thread 29 can be comprised of a spun or wound piano wire or a similar material and should be sufficiently rigid so that the tube-shaped body 10 remains in the second extended position when it is moved over the guide thread 29.

FIG. 12 shows a first embodiment of the drainage body 10. A slit 27 is formed along the body to allow urine to enter a longitudinally extending cavity within the body and to escape there through. The spherically formed ending 12 is partly shown. In the embodiment shown in FIG. 12 the stiffening wire 30 is embedded in the body 10. The stiffening wire 30 preferably should not be in a direct contact with urine.

In the alternative embodiment shown in FIG. 13 and FIG. 14 the stiffening wire 30 extends in a recess in the bottom of a longitudinally extending cavity within the body. A tongue 31 having a spherically formed tip 32 extends from an inner surface of the body 10. After insertion of the stiffening wire 30 into the recess the tongue 31 is bent over the wire 30 and pressed down into a recess 33. The recess is formed to receive and to retain the tip 32 of the tongue as shown in FIG. 14.

Figure 15:
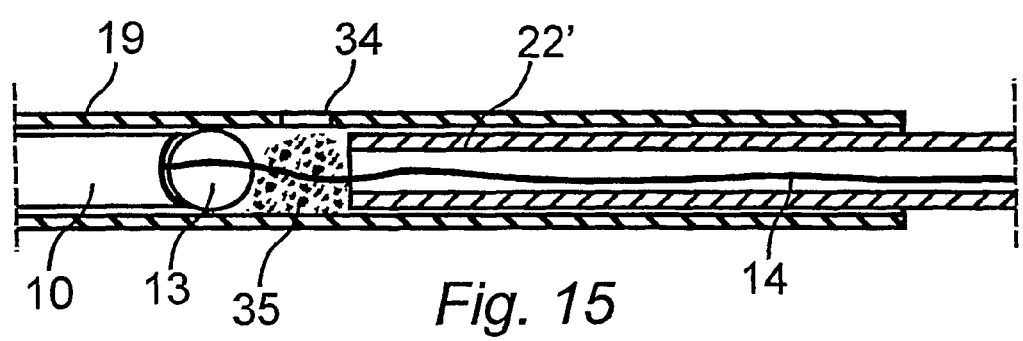
FIG. 15 shows schematically injection of a lubricant into an introducing member.

FIG. 15 shows a section of the introducing member 19 and the elongated body 10 with the soft spherical end 13 inserted therein. The driving element 22' is also inserted in the introducing member 19, a small space being left between the elongated body 10 and the driving element 22'. When the driving element 22' is advanced through the introducing member 19 it may be appropriate to facilitate the movement. An aperture 34 is formed in the introducing member 19 to allow the introduction of a lubricant 35 to the interior of the introducing member 19.

In the embodiment shown in FIG. 16 and FIG. 17 a first bowl shaped element 36 and a second bowl shaped element 37 connected by a hinge section 38 form the marker 16. A snap lock mechanism is formed by indentations 39 in the first bowl shaped element 36 and protruding elements 40 on the second bowl shaped element 37. A first cylindrical member 41 on the first bowl shaped element 36 is used to wind the thread 14 up, and a second cylindrical member 42 on the second bowl shaped element 37 will lock the thread in position when the two bowl shaped elements are pressed together.

The invention claimed is:

1. A device for the drainage of urine from a bladder to a position in a urethra past an obstruction of the urethra and then on through the urethra to an outside opening of the urethra at the outside of the human body, comprising:
   an elongated drainage body having a slit extending in a longitudinal direction along the drainage body, the slit having a length in the longitudinal direction of the drainage body exceeding the distance between the bladder and the obstruction of the urethra;
   the drainage body assuming a first contracted position taken up within the bladder and assuming a second partially extended position extending from within the bladder into the urethra and past the obstruction;
   a thread having a length sufficient to extend between at least the bladder and the outside opening, the thread connected to a first end of the drainage body to extend the drainage body from the first position to the second position upon exerting a pulling force on the thread to move the drainage body from the contracted position to the partially extended position;
   the slit of the drainage body in the second partially extended position extending from within the bladder into the urethra and downstream past the obstruction; and
   the drainage body returning to the first position upon the release of the pulling force on the thread.

2. A device in accordance with claim 1, wherein the drainage body is formed in a spiral shape in the first contracted position.

3. A device in accordance with claim 1, wherein the drainage body is folded in the first contracted position.

4. A device in accordance with claim 1, wherein the drainage body is formed of polyurethane or silicone or a similar flexible material.

5. A device in accordance with claim 1, wherein further comprising:
   an end piece having a rounded, ending form attached to a second end of the drainage body which is opposite from the first end of the elongated drainage body.

6. A device in accordance with claim 5, wherein the end piece includes a through opening communicating with the slit within the drainage body.

7. A device in accordance with claim 1, wherein the first end of the drainage body includes a soft section.

8. A device for the drainage of urine from a bladder to a position in a urethra past an obstruction of the urethra and then on through the urethra to an outside opening of the urethra to the outside of the human body, comprising:
   an elongated drainage body having an inner cavity extending in a longitudinal direction along the drainage body, the inner cavity having a length in the longitudinal direction of the drainage body exceeding the distance between the bladder and the obstruction of the urethra;
   the drainage body assuming a first contracted position taken up within the bladder and assuming a second partially extended position extending from within the bladder into the urethra and past the obstruction, the inner cavity of the drainage body in the second partially extended position extending from within the bladder into the urethra and downstream past the obstruction;
   a stiffening wire is connected to the drainage body to bias said body into said first contracted position;
   a thread having a length sufficient to extend between at least the bladder and the outside opening, the thread connected to a first end of the drainage body to extend the drainage body from the first position to the second position upon exerting of a pulling force on the thread to move the drainage body from the contracted position to the partially extended position by overcoming the bias of the stiffening wire; and the bias of the stiffening wire returning the drainage body to the first position upon the release of the pulling force on the thread.

9. A device in accordance with claim 8, wherein the drainage body has a tubular shape with an inner cavity having a length in the longitudinal direction of the drainage body exceeding the distance between the bladder and the obstruction and wherein drainage body is formed with a plurality of openings into said inner cavity.

10. A device in accordance with claim 8, wherein the drainage body includes a plurality of perforations that allow the penetration of urine into and out of the inner cavity of the drainage body.

11. A device in accordance with claim 8, wherein the stiffening wire is embedded in the drainage body.

12. A device as defined in claim 8, wherein the drainage body is formed in a spiral shape in the first contracted position.

13. A device as defined in claim 8, wherein the drainage body is folded in the first contracted position.

14. A device as defined in claim 8, wherein the inner cavity is a slit.

15. A device for the drainage of urine from a bladder to a position in a urethra past an obstruction of the urethra and then on through the urethra to an outside opening of the urethra at the outside of the human body, comprising:

an elongated drainage body having an inner cavity extending in a longitudinal direction along the drainage body. The inner cavity having a length in the longitudinal direction of the drainage body exceeding the distance between the bladder and the obstruction of the urethra, the drainage body assuming a first contracted position taken up within the bladder and assuming a second partially extended position extending from within the bladder into the urethra and downstream past the obstruction, the inner cavity of the drainage body in the second partially extended position extending from the bladder and downstream past the obstruction;

a stiffening wire connected to the drainage body to bias the drainage body into the first contracted position;

a thread having a length sufficient to extend between at least the bladder and the outside opening, the thread connected to a first end of the drainage body to extend the drainage body from the first position to the second position upon exerting a pulling force on the thread to move the drainage body from the contracted position to the partially extended position by overcoming the bias of the stiffening wire;

the bias of the stiffening wire returning the drainage body to the first position upon the release of the pulling force on the thread; and flexible tongue of the drainage body, the tongue having a spherically formed tip and being bendable to a position where the spherically formed tip is received in a longitudinally extending recess in a wall of the inner cavity to enclose the stiffening wire.

16. A method for drainage of urine from a bladder to a position in a urethra past an obstruction of the urethra at a location surrounded by a prostate gland and then on through the urethra to an outside opening of the urethra at the outside of the human body, the obstruction preventing or substantially impeding the normal passage of urine from the bladder through the urethra to the outside opening, the method comprising:

inserting into the bladder a drainage body which has an inner cavity;

allowing the drainage body to assume a first contracted position within the bladder as a result of biasing force created within the drainage body;

extending a thread attached to one end of drainage body from the bladder through the urethra and out of the outside opening;

maintaining a section of the thread extending out of the outside opening;

extending said drainage body within the bladder from the first contracted position into a second partially extended position in which the first end of the drainage body is located downstream past the obstruction and a first part of the drainage body adjacent to the first end of the drainage body and the inner cavity within the first part of the drainage body extend from the bladder through the urethra to a location downstream past the obstruction while a remaining second part of the drainage body remains contracted within the bladder;

exerting a pulling force on the extending section of the thread to extend the drainage body from the first contracted position to the second partially extended position, the extension of the drainage body from the first position to the second position occurring in opposition to the biasing force within the drainage body;

allowing urine to run through the inner cavity from the bladder past the obstruction into the urethra downstream of the obstruction and thereafter on through the urethra to the outside opening while exerting the pulling force to maintain the drainage body in the second partially extended position; and terminating the pulling force to allow the biasing force to return the first part of the drainage body back into the bladder and to return the drainage body to the first contracted position.

17. A method as defined in claim 16, wherein the inner cavity is formed by a slit extending longitudinally along at least the first part of the drainage body, and the method further comprises:

allowing urine to run through the slit.

18. A method as defined in claim 16, wherein the drainage body includes perforations in the first and second parts to allow fluid communication into and from the inner cavity, and the method further comprises:

allowing urine to flow through the perforations.

19. A method as defined in claim 16, further comprising:

allowing the drainage body to assume the first contracted position in a substantially coiled configuration.

20. A method as defined in claim 16, further comprising:

maintaining the second part of the drainage body contracted in a coiled configuration within the bladder when the drainage body is extended to the second partially extended position.

21. Apparatus for draining urine from a bladder through a bladder neck into a urethra downstream past an obstruction to the urethra at a prostate gland and into a urinary canal downstream of the prostate gland to an exterior opening of the urinary canal in a male human being, comprising:

an elongated body which normally forms into a curved shape having a spring-like characteristic which permits the body to be temporarily straightened under an outside force, the body defining a slit which extends into the body and which extends longitudinally along a slit segment of the body from one end of the body toward the other end of the body;

the spring-like characteristic of the body re-forming the body from a straightened configuration into the normal curved shape when the body is located entirely within the bladder:

the spring-like characteristic and the normal curved shape of the body restricting unintentional movement of the body through the bladder neck and into the urethra; and a thread having a sufficient length to extend from the one end of the body through the urinary canal when the body is in the normally curved shape in the bladder, the thread having a first end connected at the one end of the body to direct the one end and a portion of the slit segment through the bladder neck and into the urethra and to straighten and move the slit segment into the bladder neck and urethra in response to a pulling force applied to an outside end of the thread located at the exterior opening of the urinary canal while a portion of the slit segment remains in the bladder;

the pulling force moving the end and the slit portion of the body past the obstruction in the urethra to establish urine drainage from the bladder through the slit downstream past the obstruction and then into the urethra and the urinary canal; and the spring-like characteristic of the body withdrawing the end of the body and the slit portion from the urethra past the bladder neck and re-forming the normal curved shape of the body in the bladder upon releasing the pulling force on the thread.

22. An apparatus as defined in claim 21, wherein the other end of the elongated body includes an end piece having a rounded ending form.

23. An apparatus as defined in claim 22, wherein the end piece includes a through opening connected to the slit of the elongated body.

24. An apparatus as defined in claim 21, wherein the one end of the elongate body ends with a soft section.

25. An apparatus as defined in claim 21, further comprising:

a marker attached to the thread at a predetermined location between the ends of the thread to indicate the extent to which the pulling force should move the thread out of the urinary canal relative to the exterior opening of the urinary canal to pass urine from the bladder past the obstruction and into the urethra and the urinary canal.

* * * * *